_(12)_ United States Patent (10) Patent No.: US 7,939,053 B2
Weber et al. (45) Date of Patent: May 10, 2011

(54) METHOD OF MAKING UP NAILS

(75) Inventors: Robert Weber, Suffern, NY (US);
Karin Quissell, Clark, NJ (US)

(73) Assignee: L'Oreal S.A. (FR)

( * ) Notice: Subject to any disclaimer, the term of this patent is extended or adjusted under 35 U.S.C. 154(b) by 1062 days.

(21) Appl. No.: 11/786,629

(22) Filed: Apr. 12, 2007

(65) Prior Publication Data

US 2008/0253980 A1 Oct. 16, 2008

(51) Int. Cl.
*A61Q 3/00* (2006.01)
*A61K 8/02* (2006.01)

(52) U.S. Cl. .......................... 424/61; 424/401

(58) Field of Classification Search ............ 424/61, 424/401
See application file for complete search history.

(56) References Cited

U.S. PATENT DOCUMENTS

| | | | |
|---|---|---|---|
| 5,064,544 A * | 11/1991 | Lin et al. | 510/521 |
| 5,232,494 A | 8/1993 | Miller | |
| 5,326,388 A | 7/1994 | Miller et al. | |
| 5,464,470 A | 11/1995 | Brachman et al. | |
| 6,080,415 A * | 6/2000 | Simon | 424/401 |
| 6,124,377 A | 9/2000 | Kaiser et al. | |
| 2004/0180027 A1* | 9/2004 | Kumar et al. | 424/70.14 |
| 2004/0200496 A1* | 10/2004 | Choi | 132/200 |
| 2006/0067896 A1* | 3/2006 | Schaffer | 424/59 |
| 2006/0236470 A1 | 10/2006 | Sabnis et al. | |

* cited by examiner

*Primary Examiner* — Johann R Richter
*Assistant Examiner* — Abigail Fisher
(74) *Attorney, Agent, or Firm* — Steven Trzaska; Maria Luisa Balasta

(57) ABSTRACT

The present invention is directed to a method of making up nails, the method involving: a) applying onto the nails a first composition containing: i) at least one color precursor, ii) at least one film former, iii) at least one volatile solvent, iv) optionally, at least one buffer, and v) optionally, at least one colorant; (b) applying a second composition over top of at least a portion of the first composition, the second composition containing at least one color activator; and (c) optionally, applying a third composition over top of at least a portion of the second composition, the third composition containing at least one color deactivator.

13 Claims, No Drawings

METHOD OF MAKING UP NAILS

BACKGROUND OF THE INVENTION

Cosmetic compositions used to make up a user's nail surface must be able to impart color with ease. In the nail art, it is extremely common to coat the nail with a colored composition comprising a film former, a plasticizer, a colorant and a volatile solvent. After the evaporation of the volatile solvent, a colored film remains on the nail. While this composition provides color to the nail, the color applied cannot be changed, unless the composition is removed and replaced with a composition of a different color. Furthermore, many people like to paint multi-color designs on each nail, sometimes adding sparkles, decals, and other design elements to enhance the overall appearance of the polished nails. This is usually done by airbrushing or free hand painting, both of which require a considerable degree of skill and artistic ability. For this reason, anything beyond applying conventional nail polish to nails with a uniform color must usually be done by a professional at a nail salon.

BRIEF SUMMARY OF THE INVENTION

A first aspect of the present invention is directed to a method of making up nails involving:

(a) applying onto the nails a first composition containing: i) at least one color precursor, ii) at least one film former, iii) at least one volatile solvent, iv) optionally, at least one buffer, and v) optionally, at least one colorant;

(b) applying a second composition over top of at least a portion of the first composition, the second composition containing at least one color activator; and (c) optionally, applying a third composition over top of at least a portion of the second composition, the third composition containing at least one color deactivator.

A second aspect of the invention is directed to a cosmetic kit for making up nails comprising: i) at least one container having a composition containing: a) at least one color precursor, b) at least one film former, c) at least one volatile solvent, d) optionally, at least one buffer, and e) optionally, at least one colorant; ii) at least one container having a composition containing at least one color activator; iii) at least one container having a composition containing at least one color deactivator, and iv) optionally, means for imprinting an image onto the nails.

DETAILED DESCRIPTION OF THE INVENTION

Other than in the operating examples, or where otherwise indicated, all numbers expressing quantities of ingredients and/or reaction conditions are to be understood as being modified in all instances by the term "about".

According to one embodiment of the invention, there is provided a method of making up nails involving: a) applying onto the nails a first composition containing: i) at least one color precursor, ii) at least one film former, iii) at least one volatile solvent, iv) optionally, at least one buffer, and v) optionally, at least one colorant; (b) applying a second composition over top of at least a portion of the first composition, the second composition containing at least one color activator; and (c) optionally, applying a third composition over top of at least a portion of the second composition, the third composition containing at least one color deactivator.

First Composition
Color Precursor

A color precursor changes color upon activation by oxidation, an acidic environment, or an alkaline environment. Examples of suitable color precursors include, but are not limited to, compounds such as diarylphthalides, fluorans, indolyphthalides, acylluecoazines, leucoauramines, spiropyranes, rhodaminelactams, triarylmethanes and chromenes. Specific color precursors for use in the first composition of the present invention include, but are not limited to, those which develop a color in response to an acid, such as Spiro(12H-benzo(a)xanthene-12,1'(3'H)-isobenzofuran-3'-one,9-(diethylamino), available as COPIKEM™ 747 Red; 3-[Butyl-2-methylindol-3-yl]-3-(1-octyl-2-methylindol-3-yl)-1(3H) isobenzofuranone, available as COPIKEM™ 35 magenta; 2'-phenylamino-3'-methyl-6'-(dibutylamino)spiro isobenzofuran-1(3H),9'-(9H)-xanthen)-3-one, available as COPIKEM™ 34 Black; 3-[bis (4-octylphenyl)amino]-3-[4-(dimethylamino)phenyl]phthalide available as COPIKEM™ 14 Orange; other substituted phthalides such as that available as COPIKEM™ 7 Grape; 2'Di(phenylmethyl) amino-6'(diethylamino)spiro(isobenzofuran-1(3H),9'-(9H)xanthen)-3-one, available as COPIKEM™5 green; 3-diethylamino-6-methyl-7-anilinofluoran, available as COPIKEM™ 4 Black; 3,3-bis(1-octyl-2-methyl-1H-indol-3-yl)-1-[3H]-isobenzofuranone, available as COPIKEM™ 16 Magenta; 3,3-bis(1-butyl-2-methyl-1H-indol-3yl)-1-[3H]-isobenzofuranone available as COPIKEM™ 20 Magenta. COPIKEM is a registered trade mark of Emerald Hilton Davis, Inc.

Depending on which color precursor is chosen, it may be necessary to pre-dissolve it in a volatile solvent compatible with the solvent of the first composition, prior to its incorporation into the first composition. A suitable solvent for pre-dissolution of the color precursor is acetone.

The color precursor is generally present in the first composition in an amount ranging from about 0.01% to about 10% by weight; such as from about 0.05% to about 5% by weight; such as from about 0.1% to about 3% by weight, all weights based on the weight of the first composition.

Film Former

In the present application, the term "film former" is understood to mean a polymer capable of forming, alone or in the presence of an optional plasticizer, an isolatable film. The film former can be dissolved, or dispersed in the form of particles in the first composition.

Suitable film formers include, but are not limited to, vinyl and acrylic polymers, polyurethanes, polyesters, alkyd resins, epoxy ester resins, cellulose polymers such as nitrocellulose, cellulose esters such as cellulose acetate, cellulose acetate propionate or cellulose acetate butyrate, and mixtures thereof.

When the first composition comprises an aqueous medium, the film formers are generally present in the form of particles dispersed in the aqueous medium which form a latex or pseudolatex.

Suitable aqueous medium film-forming polymers include, but are not limited to, polyurethanes, for example anionic polyurethanes, polyester-polyurethanes, polyether-polyurethanes, radical polymers, in particular of acrylic, acrylic/styrene and/or vinyl type, polyesters or alkyd resins, or mixtures thereof.

The dispersion may also comprise an associative polymer of polyurethane type or a natural gum, such as xanthan gum.

Examples of specific aqueous medium film-forming polymers include acrylic polymers sold under the names Neocryl XK-90®, Neocryl A-1070®, Neocryl A-1090®, Neocryl BT-62®, Neocryl A-1079® or Neocryl A-523® by Zeneca or Dow Latex 432® by Dow Chemical. Also suitable are aqueous polyurethane dispersions such as the polyester-polyurethanes dispersions sold under the names "Avalure UR-405®", "Avalure UR-410®", "Avalure UR-425®" or "Sancure 2060®" by Goodrich and the polyether-polyurethanes sold under the names "Sancure 878®" by Goodrich or "Neorez R 970®" by Avecia.

The film former is generally present in the first composition of the present invention in an amount ranging from about 1% to about 40% by weight; such as from about 5% to about 30% by weight; such as from about 8% to about 25% by weight, all weights based on the weight of the first composition.

Volatile Solvent

Suitable volatile solvents are selected from hydrocarbon oils, alcohols, aldehydes, esters, ethers, ketones, silicone oils, and mixtures thereof. Preferably, the volatile solvents have a flash point of about 40° C. or less, such as less than about 25° C., such as less than about 10° C.

Examples of volatile hydrocarbon oils include, but are not limited to, volatile hydrocarbon oils having from 8 to 16 carbon atoms and mixtures thereof; branched $C_8$ to $C_{16}$ alkanes such as $C_8$ to $C_{16}$ isoalkanes (also known as isoparaffins), isododecane, isodecane, isohexadecane, and oils sold under the trade names of Isopar or Permethyl; and mixtures thereof.

Examples of volatile alcohols include, but are not limited to, ethanol; isopropanol; diacetone alcohol; 2-butoxyethanol; and mixtures thereof.

Examples of volatile aldehydes include, but are not limited to, benzaldehyde; acetaldehyde; and mixtures thereof.

Examples of volatile esters include, but are not limited to, ethyl acetate; methyl acetate; propyl acetate; n-butyl acetate; isopentyl acetate; branched $C_8$ to $C_{16}$ esters such as isohexyl or isodecyl neopentanoate; and mixtures thereof.

Examples of volatile ethers include, but are not limited to, diethyl ether; dimethyl ether; dichlorodiethyl ether; propylene glycol monomethyl ether; propylene glycol monomethyl ether acetate; dipropylene glycol mono(n-butyl) ether; and mixtures thereof.

Examples of ketones include, but are not limited to, methyl ethyl ketone; methyl isobutyl ketone; diisobutyl ketone; acetone; and mixtures thereof.

Examples of volatile silicone oils include, but are not limited to, octyltrimethicone; hexyltrimethicone; cyclopentasiloxane (D5); cyclohexasiloxane (D6); polydimethylsiloxanes having a viscosity of up to about 20 cSt; and mixtures thereof.

The volatile solvent is present in the first composition of the present invention in an amount ranging from about 30% to about 95% by weight; such as from about 50% to about 90% by weight; such as from about 60% to about 80% by weight, all weights based on the weight of the first composition.

Buffer

In an effort to preclude premature activation of the color precursor prior to application onto a nail, it may be necessary to use a buffer in the first composition. A substance is described as a buffer if it tends to resist changes due to external acid or alkaline influences. Thus, a buffer can keep the relative acidity or alkalinity of the medium in which it is contained constant, i.e., can keep its pH constant, despite the addition or formation of acids or alkalis.

The most common film former for use in nail polish compositions is nitrocellulose. It is a well known fact that the stability of nitrocellulose is much less than that of the cellulose from which it is made. The nitrate group of the nitrocellulose decomposes easily to form $NO_2$ in the presence of oxygen. Any water that is present in the first composition results in the formation of nitric acid, which will then accelerate the degradation of the nitrocellulose and cause the pH of the mixture to drop with the concomitant color change by the color precursor. The use of a buffer in the first composition thus allows the first composition to resist pH changes and to prevent premature color activation of the color precursor.

Suitable buffers are non-volatile amines that do not evaporate, examples of which include, but are not limited to, primary, secondary, tertiary, and quaternary amines.

A particularly preferred buffer for use in the present invention is aminomethyl propanol.

The buffer may be present in the first composition in an amount ranging from about 0.1% to about 3% by weight; such as from about 0.2% to about 2% by weight; such as from about 0.3% to about 1.5% by weight, all weights based on the weight of the first composition.

Colorant

The first composition of the present invention may also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. The pigments may optionally be surface-treated. Surface treatment includes, but is not limited to treatment with silicones, perfluorinated compounds, lecithin, and amino acids.

Examples of inorganic pigments for use in the present invention include, but are not limited to rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Examples of organic pigments and lakes for use in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570); and mixtures thereof.

Examples of pearlescent pigments for use in the present invention include, but are not limited to, white pearlescent pigments such as mica coated with titanium oxide, bismuth oxychloride, titanium oxychloride; colored pearlescent pigments such as titanium mica with iron oxides, titanium mica with ferric blue, chromium oxide, titanium mica with an organic pigment of the above-mentioned type as well as those based on bismuth oxychloride; and mixtures thereof.

The precise amount and type of colorant employed in the first composition of the present invention will depend on the purpose for its inclusion and, as a result, will be determined by those skilled in the art of nail polish formulation.

Second Composition

Color Activator

The second composition of the present invention contains a color activator which, when applied over top of at least a portion of the first composition containing the color precursor, results in the development of color.

Suitable color activators are those compounds capable of altering the pH of the first composition such as acids and alkalis.

Examples of suitable acids include, but are not limited to, citric acid, malic acid, gluconodeltalactone, ascorbic acid, phosphoric acid, and mixtures thereof. According to a preferred embodiment, the color activator is employed in an amount sufficient to activate the first composition containing the color precursor present on the nails.

In general, the color activator is typically dissolved in a cosmetically acceptable solvent capable of at least partially solubilizing the film formed by the first composition. One example of a cosmetically acceptable solvent is a volatile alcohol such as isopropyl alcohol.

It should be noted that a liquid-form color activator may be used so long as it is capable of partially solubilizing the film.

In general, the color activator is present in the second composition in an amount of from about 1% to about 5% by weight; such as from about 1.5% to about 4% by weight; such as from about 2% to about 3.5% by weight, all weights based on the total weight of the second composition.

Third Composition

Color Deactivator

According to another embodiment of the invention, there may be provided a third composition containing a color deactivator, used to reverse the color change imparted by the application of the second composition. More particularly, if the consumer wants to alter the aesthetic appearance of the colored nail, a color deactivator may be applied over top of at least a portion of the second composition, thereby reversing the color change on at least a portion of the nail.

Suitable color deactivators include those compounds capable of neutralizing the color activators, i.e. those compounds capable of revealing the color of the first composition. Examples of suitable color deactivators include various alkalis and acids.

The color deactivator is typically present in a cosmetically acceptable solvent such as, for example, a volatile alcohol.

In general, the color deactivator is present in the third composition in an amount of from about 0.1% to about 5% by weight; such as from about 1% to about 4% by weight; such as from about 2% to about 3.5% by weight, all weights based on the weight of the third composition.

Gelling Agents

It may be desirable to use at least one gelling agent in the compositions of the invention. The gelling agent does not encompass waxes, in the sense that it is not waxy. The gelling agent may be chosen from gelling agents in polymeric form and gelling agents in mineral form. The gelling agent may be chosen from agents that gel via chemical cross-linking and agents that gel via physical cross-linking.

Examples of suitable gelling agents include, but are not limited to, modified clays such hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox.

It should be noted that the gelling agent may be employed in pre-activated form. An example thereof is stearalkonium hectorite commercially available from Elementis under the tradename Bentone 27 V.

Other mineral gelling agents, which can be used in the invention, include silica, such as fumed silica. The fumed silica may have a particle size, which may be nanometric to micrometric, for example ranging from 5 nm to 200 nm. Silicas may be treated with a material to render them hydrophobic or hydrophilic.

Suitable treated silicas may include, but are not limited to, those sold under the names "Aerosil 130®", "Aerosil 200®", "Aerosil 255®", "Aerosil 300®", "Aerosil 380®", "Aerosil R805®", "Aerosil R972®", "Aerosil R974®", by the Degussa company, and "CAB-O-SIL HS-5®", "CAB-O-SIL EH-5®", "CAB-O-SIL LM-130®", "CAB-O-SIL MS-55®", "CAB-O-SIL M-5®", "CAB-O-SIL TS-610®", "CAB-O-SIL TS-720®", by the Cabot company.

Other gelling agents may also include modified cellulose derivatives and elastomeric organopolysiloxanes.

The at least one gelling agent, if used, will typically be present in the compositions of the present invention in an amount of from about 0.1% to about 20% by weight, such as from about 0.1% to about 15% by weight, such as from about 0.1% to about 10% by weight, all weights based on the weight of each individual composition.

Additives/Auxiliary Agents

The compositions may further comprise at least one cosmetically or dermatologically acceptable additive/auxiliary agent. Suitable additives/auxiliary agents include, but are not limited to, plasticizers, antioxidants, essential oils, preservatives, fragrances, emollients, moisturizers, fillers, pasty fatty substances, waxy fatty substances, non-volatile polar solvents, non-volatile non-polar solvents, neutralizing agents, and polymers.

Typically, the additives/auxiliary agents may be present in amounts ranging from about 0.01% to about 20% by weight; such as from about 0.1% to about 10% by weight; such as from about 0.5% to about 5% by weight, all weights based on the weight of each individual composition.

Active Agents

The compositions of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. What is a safe and effective amount of the active ingredient will vary with the specific active agent, the ability of the active agent to penetrate through the skin, the age, health and skin condition of the user, and other like factors.

Suitable active agents may include, but are not limited to, emollients, moisturizers, vitamins and essential fatty acids.

Typically, the active ingredient may be present in amounts ranging from about 0.001% to about 20% by weight; such as from about 0.1% to about 10% by weight; such as from about 0.5% to about 5% by weight, all weights based on the weight of the individual compositions.

The compositions of the present invention may also contain sunscreens which typically comprise chemical absorbers, physical blockers, and mixtures thereof.

Suitable chemical absorbers include, but are not limited to, p-aminobenzoic acid derivatives, anthranilates, benzophenones, camphor derivatives, cinnamic derivatives, dibenzoyl methanes (such as avobenzone also known as Parsol 1789), diphenylacrylate derivatives, salicylic derivatives, triazine derivatives, benzimidazole compounds, bis-benzoazolyl derivatives, methylene bis-(hydroxyphenylbenzotriazole) compounds, sunscreen polymers, silicone based absorbers, and mixtures thereof.

Suitable physical blockers include, but are not limited to, cerium oxides, chromium oxides, cobalt oxides, iron oxides, red petrolatum, silicone-treated titanium dioxide, titanium dioxide, zinc oxide, zirconium oxide, and mixtures thereof.

According to another embodiment of the invention, there is provided a cosmetic kit for making up nails which includes: (a) at least one container comprising a first composition containing: i) at least one color precursor, ii) at least one film former, iii) at least one solvent, iv) optionally at least one buffer, and, v) optionally, at least one colorant; b) at least one container comprising a second composition containing at least one color activator; (c) optionally, at least one container comprising a third composition containing at least one color deactivator, and, (d) optionally, means for imprinting an image onto the nails.

Means for Imprinting an Image onto the Nails

Any device capable of imprinting an image onto the nails may be used without departing from the spirit of the invention. One example of such a device is an ink pad stamp having a pattern/design protruding therefrom. The pattern/design may be removably affixed so that a variety of design choices are provided.

The ink pad stamp is impregnated with either the second or third composition, and may be pressed onto either the first or second composition.

This type of device facilitates the presence of various types of designs onto the nail, as well as the appearance of a French manicure.

In the event the user wishes to remove the design from the nail, a deactivator composition in accordance with the present invention may be employed to remove said design.

The present invention is further described in terms of the following non-limiting examples. Unless otherwise indicated, all parts and percentages are on a weight-by-weight percentage basis.

EXAMPLES

Color precursor composition

| Ingredient | w/w % |
|---|---|
| Film formers | 14.00 |
| Plasticizers | 5.00 |
| Volatile solvent | 79.00 |
| 3,3-Bis(2-Methyl-1-Octyl-1h-Indol-3-Yl)Phthalide (color precursor) | 0.50 |
| Aminomethyl Propanol | 0.40 |
| Pigments/fillers | 1.00 |
| Gelling agent | 0.10 |
| Total | 100 |

Color activator composition

| Ingredient | % w/w |
|---|---|
| Isopropyl alcohol | 96 |
| Citric acid | 4 |
| Total | 100 |

Color Deactivator Composition:

| Ingredient | % w/w |
|---|---|
| Isopropyl alcohol | 95 |
| amino methyl propanol | 5 |
| Total | 100 |

It is to be understood that the foregoing describes preferred embodiments of the invention and that modifications may be made therein without departing from the spirit or scope of the invention as set forth in the claims.

What is claimed is:

1. A method of making up nails comprising:
   a) applying onto the nails a first composition comprising:
      i) at least one color precursor;
      ii) at least one film former;
      iii) at least one volatile solvent;
      iv) optionally, at least one buffer; and,
      v) optionally, at least one colorant;
   b) applying a second composition over top of at least a portion of the first composition, the second composition comprising at least one color activator; and
   c) optionally, applying a third composition over top of at least a portion of the second composition, the third composition comprising at least one color deactivator.

2. The method according to claim 1, wherein the color precursor is present in an amount ranging from about 0.01% to about 10% by weight, based on the weight of the first composition.

3. The method according to claim 1, wherein the color precursor is present in an amount ranging from about 0.1% to about 3% by weight, based on the weight of the first composition.

4. The method according to claim 1, wherein the film former is present in an amount ranging from about 1% to about 40% by weight, based on the weight of the first composition.

5. The method according to claim 1, wherein the film former is present in an amount ranging from about 8% to about 25% by weight, based on the weight of the first composition.

6. The method according to claim 1, wherein the film former is a cellulose polymer.

7. The method according to claim 1, wherein the volatile solvent is present in an amount ranging from about 30% to about 95% by weight, based on the weight of the first composition.

8. The method according to claim 1, wherein the volatile solvent is present in an amount ranging from about 60% to about 80% by weight, based on the weight of the first composition.

9. The method according to claim 1, wherein the buffer is present in an amount ranging from about 0.1% to about 3% by weight, based on the weight of the first composition.

10. The method according to claim 1, wherein the buffer is present in an amount ranging from about 0.3% to about 1.5% by weight, based on the weight of the first composition.

11. The method according to claim 1, wherein the buffer is aminomethyl propanol.

12. The method according to claim 1, wherein the color activator is an organic acid.

13. The method according to claim 1, wherein the color activator is citric acid.

* * * * *